(12) United States Patent
Fukuchi

(10) Patent No.: US 6,221,896 B1
(45) Date of Patent: Apr. 24, 2001

(54) INSECTICIDAL AND MITICIDAL COMPOSITIONS

(75) Inventor: Toshiki Fukuchi, Yokohama (JP)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/308,846

(22) PCT Filed: Nov. 25, 1997

(86) PCT No.: PCT/JP97/04273

§ 371 Date: May 24, 1999

§ 102(e) Date: May 24, 1999

(87) PCT Pub. No.: WO98/23153

PCT Pub. Date: Jun. 4, 1998

(30) Foreign Application Priority Data

Nov. 25, 1996 (JP) .................................................. 8-313570

(51) Int. Cl.⁷ .......................... A01N 43/32; A01N 43/36; A01N 43/02; A01N 47/10; A01N 47/28

(52) U.S. Cl. .......................... 514/427; 514/431; 514/479; 514/483; 514/518; 514/587; 514/435

(58) Field of Search ..................... 514/427, 431, 514/479, 483, 435, 518, 587

(56) References Cited

U.S. PATENT DOCUMENTS 5,187,184 * 2/1993 Lovell .................................. 514/406

FOREIGN PATENT DOCUMENTS 0 492 125 A1 7/1992 (EP) .

* cited by examiner

*Primary Examiner*—Allen J. Robinson
(74) *Attorney, Agent, or Firm*—Barbara L. Renda; Barbara V. Maurer

(57) ABSTRACT

This invention relates to an insecticidal and miticidal composition which contains as active ingredients chlorfenapyr in combination with one or more compounds selected from the group consisting of benzoepin, nereistoxin-type insecticidal agents and diafenthiuron.

10 Claims, No Drawings

INSECTICIDAL AND MITICIDAL COMPOSITIONS

This application is a 371 of PCT/JP97/04273, filed Nov. 25, 1997.

DESCRIPTION

1. Field of the Invention

This invention relates to insecticidal and miticidal compositions which contain as active ingredients 4-bromo-2-(4-chlorophenyl)-1-(ethoxymethyl)-5-(trifuloromethyl)pyrrole-3-carbonitrile (hereinafter referred to as chlorfenapyr) in combination with a second insecticidal and miticidal ingredient(s) which can be effectively applied especially in the agrohorticultural field.

2. Background of the Invention

Chlorfenapyr, which is an active ingredient of the insecticidal and miticidal composition of the invention, is known to be effective against insects such as Hemiptera pests such as leafhoppers (Doltocephalidae), Lepidoptera pests such as diamond back moth (*Plutella xylostella*), common cutworm (*Spodoptera litura*) and apple leafminer (*Phyllonorycter ringoniella*) and Thysanoptera pests such as *Thrips palmi* and yellow tea thrips (*Spirtothrips dorsalis*) and agrohorticultural pests such as mites such as two-spotted spider mite (*Tetranychus urticae koch*), Kanzawa spider mite (*Tetranychus kanzawai kishida*) and *Aculops pelekassi*.

The second active ingredient of the insecticidal and miticidal composition of the invention includes one or more of the following compounds: hexachlorohexahydromethanobenzodioxathiepine oxide [benzoepin (endosulfan)]; Nereistoxin-type insecticidal agents such as 1,3-bis-(carbamoylthio)-2-(N,N-dimethyl-amino)propane hydrochloride (cartap), 5-dimethyl-amino-1,2,3-trithiane oxalate (thiocyclam) and the like; and 1-tert-butyl-3-(2,6-diisopropyl-4-phenoxyphenyl)-thiourea (diafenthiuron), all of which are known to be effective agents against agricultural pests such as Hemiptera, Lepidoptera and Coleoptera insects.

Although insecticidal and miticidal agents have been developed in order to control various pests such as agrohorticultural pests or hygienic pests and in practice have been used as a single or a mixed agent, pests which have acquired resistance against various agents have been appearing as a result of the repeated use of these agents.

In particular, important economic pests in agrohorticulture such as Tetranychidae, which have a propensity to easily develop resistance against pesticidal agents due to their ability to deposit large numbers of eggs and produce large numbers of generations which, themselves, require only a few days for development are of great concern. Resistance development in this pest family is also favored by a high mutation rate and frequent inbreeding, due to minimal migration. For these reasons, two-spotted spider mite (*Tetranychus urticae koch*), Kanzawa spider mite (*Tetranychus kanzawai kishida*), *Aculops pelekassi*, and the like have acquired resistance, to some degree, against almost all existing pesticidal agents. Therefore, in order to prevent and control the damage caused by Tetranychidae, development of a new insecticidal and miticidal agent which shows a high effect against Tetranychidae which have acquired resistance against the conventional miticidal agents is highly desirable.

However, to obtain an insecticidal and miticidal composition which shows no cross-resistance with existing insecticidal and miticidal agents, has no toxicity problems and has little negative impact on the environment, is extremely difficult. Therefore, a means to delay or prevent the development of resistant strains of pest species is always being sought. In order to apply an effective agent as long as possible, a rotational application of agents with different mechanisms of action is adopted for good pest management practice. However, this approach does not necessarily give satisfactory pest control. Therefore, after a resistance problem has occurred, a countermeasure to resistance by combining insecticidal and miticidal agents has been studied. However, a high synergistic action has not always been found.

Therefore, it is an object of this invention to provide an insecticidal and miticidal composition which demonstrates a high controlling effect even against Tetranychidae which have acquired resistance against chlorfenapyr.

SUMMARY OF THE INVENTION

In order to establish a countermeasure to a resistance problem in Tetrachychidae against chlorfenapyr before such a problem occurs, the synergistic action with the existing insecticidal, miticidal and fungicidal agents was studied using resistant species which have been artificially established in the laboratory by selecting Tetrachychidae which have been treated with chlorfenapyr. Thus, it has now been found that an insecticidal and miticidal composition which contains as active ingredient chlorfenapyr in combination with one or more compounds selected from the group consisting of benzoepin, nereistoxin-type insecticidal agents and diafenthiuron shows a joint action or synergistic effect which could not be foreseen from each individual ingredient alone.

DETAILED DESCRIPTION OF THE INVENTION

Chlorfenapyr, which is an active ingredient of the insecticidal and miticidal composition of the invention, is a known compound (Japanese Laid-open (Kokai) Patent Publication.No. 104042/89). Compounds which are suitable for use as the second active ingredient in the composition of the invention such as one or more of the following compounds:

1) Benzoepin (6,7,8,9,10,10-hexachloro- 1,5,5a, 9,9a-hexahydro-6,9-methano-2,4.3-benzodioxathiepin-3-oxide),
2) Nereistoxin-type insecticidal agents such as Cartap (1,3-bis(carbamoylthio)-2-(N,N-dimethylamino) propane hydrochloride), Thiocyclam (5-dimethylamino-1,2,3-trithiane oxalate) and Bensultap (S,S'-2-dimethylaminotrimethylene-di (benzenethiosulfonate), preferably cartap and thiocyclam, and
3) Diafenthiuron (1-tert-butyl-3-(2,6-diisopropyl-4-phenoxyphenyl)thiourea)

(hereinafter referred to as Group A) are all known compounds and are commercial products which are readily available.

For the preparation of the insecticidal and miticidal composition of the invention, it is suitable to formulate as a wettable powder, aqueous concentrate, emulsion, liquid concentrate, sol (flowable agent), powder, aerosol, or the like, by conventional methods such as admixing chlorfenapyr and one or more compounds of Group A with a suitable carrier and auxilliaries, such as emulsifiers, dispersants, stabilizers, suspending agents, penetrants, and the like.

The content of the total active ingredients of the composition of the invention, expressed as weight/weight %, is preferably in the range of about 1–90% for wettable powder, aqueous concentrate, emulsion, liquid concentrate and sol formulations. The preferable content of total active ingredients is about 0.5–10% for powder formulations and about 0.01–2% for aerosol formulations.

Carriers suitable for use in the insecticidal and miticidal compositions of the invention may be any solid or liquid carrier which is commonly used for an agrohorticultural composition. Various surfactants, stabilizers and other auxiliary ingredients may be used according to the necessity. In commercially useful formulations, the composition of the invention may also be present in a mixture with other active agents, for example various insecticidal, miticidal, fungicidal and herbicidal agents, plant growth regulators, repellants, attractants, synergists and fertilizers and fragrances, in order to expand its applicability.

The ratio of chlorfenapyr to the compound(s) of Group A in the insecticidal and miticidal composition of the invention is about 1 weight part of chlorfenapyr to about 0.01–100 weight parts, preferably about 1–20 weight parts, of a compound(s) of Group A.

The insecticidal and miticidal composition of the invention is particularly effective for the control of Tetranychidae such as two-spotted spider mite (*Tetranychus urticae koch*), *Tetranychus cinnabarinus* (boisduyal), Kanzawa spider mite (*Tetranychus Kanzawai kishida*), *Tetranichus viennensis zacher*, and the like.

Advantageously, the insecticidal and miticidal composition of the invention shows not only a synergistic miticidal effect against the above-mentioned Tetranychidae, but also demonstrates simultaneous control of troublesome pests such as leafroller moths (Tortricidae), Carposinidae, leafminer moths (Lyonetiidae), plant bugs (Pentatomidae), aphids (Aphididae), leafhoppers (Deltociphalidae), thrips (Thripidae), aphids (Aphididae), diamond back moths (Plutella xylostella), *Mamestra brassicae*, leaf beetles (Chrysomelidae), whiteflies (Aleyrodidae) and the like on important agronomic crops such as fruit trees, for example citrus, apple and pear; tea plants; vegetables and the like.

Although the application amount may differ according to prevailing conditions such as the population density, the kinds and cultivation form of the target crop, the weather conditions, the manner of application, and the like, in general, the total amount of chlorfenapyr in combination with the compound(s) of Group A is about 0.1–1,000 g, preferably about 40–500 g per 10 ares. In actual practice, the composition of the invention when in the form of a wettable powder, aqueous concentrate, emulsion, liquid concentrate, sol, or the like may be diluted with water and applied to the crop at an application rate of about 100–700 liters per 10 ares. When the inventive composition is formulated as a powder or aerosol, the crop may be treated with the undiluted formulation.

The insecticidal and miticidal composition of the invention is further illustrated in the examples set forth hereinbelow. These examples are not intended to limit the scope of the invention.

EXAMPLE 1

FORMULATION EXAMPLE 1 EMULSION

| | |
|---|---|
| Clorfenapyr | 5 parts |
| Benzoepin | 40 parts |
| Xylene | 25 parts |
| Dimethyl formamide | 20 parts |
| Sorpol 3005X | 10 parts |

(Polyoxyethylene type surfactant manufactured by Toho Chemical Industry Co., Ltd., commercial name)

An emulsion is obtained by mixing homogeneously and dissolving the above-mentioned ingredients.

EXAMPLE 2

FORMULATION EXAMPLE 2 WETTABLE POWDER

| | |
|---|---|
| Chlorfenapyr | 5 parts |
| Thiocyclam | 50 parts |
| Carplex #80 | 10 parts |
| (White carbon manufactured by Shionogi & Co., Ltd, commercial name) | |
| Zeeklite SP | 22 parts |
| (Mixture of kaolinite and cericite manufactured by Zeeklite Ind., commercial name) | |
| Calcium ligninsulfonate | 8 parts |

A wettable powder is obtained by homogeneously mixing the above-mentioned ingredients by jet air mill.

EXAMPLE 3

FORMULATION EXAMPLE 3 SOL (FLOWABLE AGENT)

| | |
|---|---|
| Chlorfenapyr | 5 parts |
| Diafenthiuron | 25 parts |
| Ethylene glycol | 8 parts |
| Sorpol AC3020 | 5 parts |
| (Toho Chemical Ind. Co., Ltd., commercial name) | |
| Xanthan gum | 0.1 parts |
| Water | 56.9 parts |

Chlorfenapyr, diafenthiuron and a previously prepared mixture of ethylene glycol, Sorpol AC3020 and xanthan gum are well mixed in water and dispersed. This slurry is then wet pulverized by Dynomill (Shinmaru Enterprises) to obtain a sol (flowable agent).

EXAMPLE 4
FORMULATION EXAMPLE 4 POWDER

| | |
|---|---|
| Chlorfenapyr | 0.5 parts |
| Cartap | 3.5 parts |
| White carbon | 5.0 parts |
| Clay | 91 parts |
| (Nippon Talc Co., Ltd.) | |

The above-mentioned ingredients are homogeneously mixed and pulverized to obtain a powder Each of the above-prepared formulations is suitable to be used as an agrochemical.

EXAMPLE 5
TEST EXAMPLE I

In this experiment, the miticidal effect against female imagines (adults) of Kanzawa spider mite (*Tetranychus kanzawai kishida*) which are resistant to chlorfenapyr is evaluated.

Round leaf disks (2 cm diameter) are cut out of a first leaf of kidney bean by a leaf punch and 4 sheets of the disks are placed on wet sanitary cotton in a plastic cup (8 cm diameter). On each leaf disk, 4 female imagines of Kanzawa spider mite (*Tetranychus kanzawai kishida*) which had acquired a strong resistance to chlorfenapyr are inoculated.

After the inoculation, chlorfenapyr and a compound(s) selected from group A are dispersed in water containing 200 ppm of an extender (Sorpol 3005x) and diluted such that a predetermined concentration of active ingredient is obtained. Each plastic cup is sprayed with 3.5 ml of a test solution with a rotary spray tower (Mizuho Scientific Co., Ltd.) and stored in a constant temperature chamber held at 25°±1° C. (32 individuals are tested per concentration, 4–5 concentrations are evaluated per formulation and 2 performances are repeated). Two days after treatment, the number of living and dead female imagines of Kanzawa spider mite (*Tetranychus kanzawai kishida*) which had acquired a strong resistance to chlorfenapyr is counted and the mortality (%) is calculated according to the formula shown hereinbelow.

$$\text{Mortality } (\%) = \frac{\text{Number of dead mite}}{\text{Number of alived mite} + \text{Number of dead mite}} \times 100$$

Using these data, the $LC_{50}$ values are obtained by conventional probit analysis techniques. A co-toxicity coefficient is calculated by applying Sun and Johnson's formula (J. Econ. Ent., Vol 53, p. 887, 1980) which is generally used to determine the degree of synergistic activity.

The $LC_{50}$ value of each individual effective ingredient which constitutes the insecticidal and miticidal composition of the invention is shown in Table I. The $LC_{50}$ values and the co-toxicity coefficients of the composition of the invention are shown in Table II.

Co-toxicity coefficient=$T^c$ $$T^c = \frac{\text{Actual toxicity index of mixture}}{\text{Theoretical toxicity index of mixture}} \times 100$$

For $T^c$ values greater than 100, the greater value indicates a stronger synergistic action. For a $T^c$ value equal to 100, an additive action is indicated. For $T^c$ values less than 100, the lesser value indicates a greater antagonistic action. A more detailed description of the calculation of the co-toxicity coefficient using the above-referenced Sun and Johnson formula follows.

The $LC_{50}$ values of Test Compound A alone and Test Compound B alone and the $LC_{50}$ value of the (A+B) mixture M is determined.

Actual toxicity index of mixture M=$M^{ti}$

Each $LC_{50}$ value of effective ingredient A and effective ingredient B and the $LC_{50}$ value of the mixture of A+B are used to determine the actual toxicity index as shown in the equation below.

$$M^{ti} = \frac{LC_{50} \text{ of } A}{LC_{50} \text{ of } M} \times 100$$

Theoretical toxicity index of mixture M=$Th.M^{ti}$ $Th.M^{ti}$=(Toxicity index of A×% A in M+Toxicity index of B×% B in M)

Toxicity index of B=$B^{ti}$ $$B^{ti} = \frac{LC_{50} \text{ of } A}{LC_{50} \text{ of } B} \times 100$$

Toxicity index of A=$A^{ti}$ $A^{ti}$=100

TABLE I

Evaluation Of The Effect Of Test Compounds Against Female Imago Of Kanzawa Spider Mite Which Have Acquired Resistance Against Chlorfenapyr

| TEST COMPOUND | $LC_{50}$ (ppm) |
|---|---|
| Chlorfenapyr | 1500 |
| Benzoepin | 600 |
| Cartap | 2300 |
| Thiocyclam | 230 |
| Diafenthiuron | 540 |

By comparison, the $LC_{50}$ value for chlorfenapyr against a susceptible strain of spider mite is about 5 ppm.

As can be seen from the data on Table I, the resistant strain of Kanzawa spider mite which was obtained by a long artificial selection procedure against chlorfenapyr in a laboratory on a colony of Kanzawa spider mite which had been collected in the field, has developed about a 300-fold resistance to chlorfenapyr.

In the case of benzoepin, cartap, thiocyclam and diafenthiuron, this Kanzawa spider mite is thought to originate from a colony which had acquired resistance to these insecticidal agents prior to the time of collection in the field. These compounds all showed low effects.

TABLE II

Evaluation Of The Effect Of Test Mixtures Against Female Imago Of Kanzawa Spider Mite Which Have Acquired Resistance Against Chlorfenapyr

| TEST MIXTURE | RATIO[1] | $LC_{50}$ ppm) | $T^c$ |
| --- | --- | --- | --- |
| Chlorfenapyr + Benzoepin | 1:12 | 230 | 270 |
| Chlorfenapyr + cartap | 1:10 | 230 | 950 |
| Chlorfenapyr + Thiocyclam | 1:10 | 230 | 110 |
| Chlorfenapyr + Diafenthiuron | 1:10 | 540 | 110 |

[1]Chlorfenapyr: Second active Ingredient
$T^c$ = Co-tonicity Coefficient

As can be seen from the data on Table II, the co-toxicity coefficient of the test mixtures is a value greater than 100, which is indicative of strong synergistic action.

What is claimed is:

1. An insecticidal and miticidal composition which contains as active ingredients synergistically effective amounts of chlorfenapyr in combination with one or more compounds selected from the group consisting of benzoepin, nereistoxin-type insecticidal agents and diafenthiuron.

2. The composition according to claim 1 wherein the active ingredients comprise chlorfenapyr in combination with one or more nereistoxin-type insecticidal agents.

3. The composition according to claim 2 wherein the nereistoxin-type insecticidal agent is cartap or thiocyclam.

4. The composition according to claim 1 wherein the active ingredients comprise chlorfenapyr in combination with benzoepin.

5. The composition according to claim 1 wherein the active ingredients comprise chlorfenapyr in combination with diafenthiuron.

6. The composition according to claim 1 wherein the chlorfenapyr is present in a ratio of about 1 weight part to about 0.01–100 total weight parts of one or more compounds selected from the group consisting of benzoepin, cartap, thiocyclam and diafenthiuron.

7. The composition according to claim 6 wherein the ratio is about 1 weight part of chlorfenapyr to about 1–20 weight parts of one or more compounds selected from the group consisting of benzoepin, cartap, thiocyclam and diafenthiuron.

8. A process for the preparation of a composition of claim 1 which comprises admixing the active ingredients with an agrohorticulturally acceptable solid or liquid carrier.

9. The process according to claim 8 wherein the active ingredients comprise chlorfenapyr in combination with one or more compounds selected from the group consisting of benzoepin, cartap, thiocyclam and diafenthiuron.

10. The process according to claim 9 wherein the chlorfenapyr is present in a ratio of about 1 weight part to about 1–20 weight parts of one or more compounds selected from the group consisting of benzoepin, cartap, thiocyclam and diafenthiuron.

* * * * *